(12) United States Patent
Song

(10) Patent No.: US 11,224,674 B2
(45) Date of Patent: Jan. 18, 2022

(54) ESSENTIAL OIL ATOMIZER

(71) Applicant: PUZHEN LIFE CO., LIMITED, Shatin (HK)

(72) Inventor: Baojie Song, New York, NY (US)

(73) Assignee: PUZHEN LIFE CO., LIMITED, Hong Kong (HK)

( * ) Notice: Subject to any disclaimer, the term of this patent is extended or adjusted under 35 U.S.C. 154(b) by 0 days.

(21) Appl. No.: 16/895,967

(22) Filed: Jun. 8, 2020

(65) Prior Publication Data

US 2020/0297888 A1    Sep. 24, 2020

Related U.S. Application Data

(63) Continuation-in-part of application No. 16/526,500, filed on Jul. 30, 2019, and a continuation-in-part of application No. 16/033,037, filed on Jul. 11, 2018, now Pat. No. 11,123,757, which is a continuation-in-part of application No. PCT/CN2018/081092, filed on Mar. 29, 2018, and a continuation-in-part of application No. PCT/CN2018/081091, filed on Mar. 29, 2018.

(60) Provisional application No. 62/755,099, filed on Nov. 2, 2018.

(51) Int. Cl.
| | |
|---|---|
| *A61L 9/14* | (2006.01) |
| *B05B 7/04* | (2006.01) |
| *B05B 7/24* | (2006.01) |
| *B05B 7/32* | (2006.01) |
| *B05B 7/00* | (2006.01) |

(52) U.S. Cl.
CPC .............. *A61L 9/14* (2013.01); *B05B 7/0075* (2013.01); *B05B 7/0483* (2013.01); *B05B 7/2491* (2013.01); *B05B 7/32* (2013.01); *A61L 2209/134* (2013.01)

(58) Field of Classification Search
CPC ......... A61L 9/03; A61L 9/14; A61L 2209/134
See application file for complete search history.

(56) References Cited

U.S. PATENT DOCUMENTS

| | | | |
|---|---|---|---|
| 3,866,414 | A | 2/1975 | Bahr |
| 4,184,615 | A | 1/1980 | Wright |
| 4,550,706 | A | 11/1985 | Hoffman |
| 4,974,573 | A | 12/1990 | Jensen |
| 7,878,418 | B2 | 2/2011 | Sevy |
| 8,857,735 | B2 | 10/2014 | Rosener et al. |

(Continued)

FOREIGN PATENT DOCUMENTS

| | | |
|---|---|---|
| CN | 2751868 Y | 1/2006 |
| CN | 201832737 U | 5/2011 |

(Continued)

OTHER PUBLICATIONS

European Search Report dated Sep. 21, 2021 as received in EP Application No. 21178259.4.

(Continued)

*Primary Examiner* — Sean E Conley
(74) *Attorney, Agent, or Firm* — Dorsey & Whitney LLP

(57) ABSTRACT

An essential oil reflux-type atomizer comprising the following structures: a chassis, housing, atomization chamber, gas pump, gas tube, gas nozzle, oil nozzle, and filter atomization mechanism. Oil and gas flow together at the gas and oil nozzles to disperse and atomize the oil in the gas flow.

19 Claims, 5 Drawing Sheets

(56) References Cited

U.S. PATENT DOCUMENTS

| | | | |
|---|---|---|---|
| 9,211,357 B1 | 12/2015 | Li | |
| 9,358,557 B2 | 6/2016 | Young et al. | |
| 9,415,130 B2 | 8/2016 | Sevy | |
| 9,421,295 B1* | 8/2016 | Li | A61L 9/125 |
| 2002/0068023 A1 | 6/2002 | Davis | |
| 2003/0132311 A1 | 7/2003 | Dorendorf et al. | |
| 2005/0116059 A1 | 6/2005 | Lin | |
| 2006/0145368 A1 | 7/2006 | Thomas | |
| 2007/0163577 A1 | 7/2007 | Van | |
| 2007/0242464 A1 | 10/2007 | Yu et al. | |
| 2008/0121660 A1* | 5/2008 | Ophardt | A47K 5/16 222/190 |
| 2011/0259974 A1 | 10/2011 | Cooper et al. | |
| 2016/0000959 A1* | 1/2016 | Sevy | A61L 9/14 422/4 |
| 2016/0361678 A1 | 12/2016 | Blackley | |
| 2017/0246336 A1 | 8/2017 | Suissa et al. | |
| 2019/0275186 A1 | 9/2019 | Hsiao | |
| 2019/0299230 A1 | 10/2019 | Song | |
| 2020/0016344 A1 | 1/2020 | Scheck et al. | |
| 2020/0022411 A1* | 1/2020 | Krietzman | A24F 47/008 |
| 2020/0139387 A1 | 5/2020 | Song | |

FOREIGN PATENT DOCUMENTS

| | | |
|---|---|---|
| CN | 202184967 U | 4/2012 |
| CN | 202741276 U | 2/2013 |
| CN | 103041480 A | 4/2013 |
| CN | 103230638 A | 8/2013 |
| CN | 103375230 A | 10/2013 |
| CN | 203436642 U | 2/2014 |
| CN | 203916959 U | 11/2014 |
| CN | 204072864 U | 1/2015 |
| CN | 204072868 U | 1/2015 |
| CN | 204396240 U | 6/2015 |
| CN | 105013059 A | 11/2015 |
| CN | 107758798 A | 3/2016 |
| CN | 105536021 A | 5/2016 |
| CN | 105561367 A | 5/2016 |
| CN | 106423613 A | 2/2017 |
| CN | 205966339 U | 2/2017 |
| CN | 206046319 U | 3/2017 |
| DE | 202019104768 U1 | 8/2019 |
| EP | 2409716 A2 | 1/2012 |
| TW | 411243 S | 11/2000 |
| WO | 2013030117 A2 | 3/2013 |

OTHER PUBLICATIONS

European Search Report dated Sep. 20, 2021 as received in EP Application No. 21171675.8.
European Search Report dated Oct. 21, 2021 as received in EP Application No. 21178262.8.

* cited by examiner

ESSENTIAL OIL ATOMIZER

CROSS-REFERENCE TO RELATED APPLICATIONS

The present disclosure is a continuation-in-part of U.S. patent application Ser. No. 16/033,037, filed 11 Jul. 2018, now U.S. Pat. No. 11,123,757, which is a continuation-in-part of PCT/CN2018/081092 filed 29 Mar. 2018 and a continuation-in-part of PCT/CN2018/081091, filed 29 Mar. 2018. The present disclosure is also a continuation-in-part of U.S. patent application Ser. No. 16/526,500, filed 30 Jul. 2019, which claims priority to U.S. Provisional Patent Application No. 62/755,099, filed 2 Nov. 2018. The contents of the entire above-mentioned patent applications are hereby incorporated by reference.

TECHNICAL FIELD

The present disclosure relates to the field of atomizers, and more particularly to an airflow guided essential oil reflux-type atomizer.

BACKGROUND

In daily life, essential oils are often used to improve the surrounding environment or to perform medical treatment, such as sterilization, disinfection or changing environmental odor, etc. When using the essential oils, an atomizer is often used to atomize the essential oils for facilitating diffusion of the essential oils into the environment.

SUMMARY

One aspect of the present disclosure relates to an essential oil atomizer comprising a housing configured to connect to an oil receptacle, wherein the housing can have an outlet opening, a nozzle assembly configured to be in fluid communication with a gas source and configured to be in fluid communication with oil in the oil receptacle to atomize the oil with gas from the gas source, and a cover movable between a first position in which the outlet opening is unsealed and a second position in which the outlet opening is sealed by the cover.

In some embodiments, the atomizer can further comprise the gas source, which can comprise a gas pump, and an energy source positioned in the housing and electrically connected to the gas pump. Gas emitted from the gas pump can be configured to pass through the nozzle assembly to atomize oil in the nozzle assembly, and atomized oil and gas can be movable through the outlet opening when the cover is in the first position. In some embodiments, the cover can comprise a plunger portion insertable into the outlet opening. The cover can comprise an outer shell portion surrounding a portion of the housing when the cover is in the second position. An inner cover can be positioned on a portion of the housing bearing the outlet opening. At least one of the outlet opening and the cover can be configured to deform when the outlet opening is sealed. The nozzle assembly can comprise an inlet, wherein a one-way valve is configured to prevent gas or oil flow through the inlet.

Another aspect of the disclosure relates to an essential oil atomizer comprising a housing, a nozzle assembly having an oil inlet configured to connect to an oil source and a gas inlet configured to connect to a gas source, and a one-way valve configured to prevent fluid flow through the oil inlet or the gas inlet.

The atomizer may further comprise the gas source, wherein the gas source can comprise a gas pump positioned in the housing, and an energy source positioned in the housing and electrically connected to the gas source. The nozzle assembly can comprise an oil nozzle connected to the oil inlet and a gas nozzle connected to the gas inlet, with the gas nozzle configured to output gas across the oil inlet to atomize oil at the oil nozzle, and atomized oil and gas can be movable through an outlet in the housing. The atomizer can further comprise the gas source connected to the gas inlet, with the gas source configured to supply gas through the one-way valve. The one-way valve can be a check valve or a duckbill valve. The one-way valve can be positioned in the gas inlet. The one-way valve can be configured to prevent fluid flow of oil from the oil source through the gas inlet. The atomizer can also further comprise a cover, wherein the housing comprises an outlet, with the cover being configured to seal fluid communication through the outlet.

Yet another aspect of the disclosure relates to an essential oil atomizer, comprising a housing having a first end, a second end positioned opposite the first end, and an outlet opening through the first end, and a nozzle assembly positioned in the housing and comprising a gas nozzle and an oil nozzle, with the gas nozzle being configured to expel gas toward the second end. Oil in the oil nozzle can be configured to be atomized by gas from the gas nozzle and to pass through the outlet of the housing.

In some embodiments, the atomizer can further comprise a gas pump located in the housing and connected to the gas nozzle, a cover configured to reversibly seal the outlet at the first end, and a valve preventing fluid flow from the oil nozzle to the gas pump. The housing can be attachable to an oil receptacle with the gas nozzle and the oil nozzle at least partially within the oil receptacle. The gas nozzle can be oriented substantially perpendicular to the oil nozzle. The atomizer can also further comprise a valve to prevent fluid flow through an inlet of the nozzle assembly. The oil nozzle can comprise an oil outlet having a substantially horizontal longitudinal axis.

The above summary of the present invention is not intended to describe each embodiment or every implementation of the present invention. The Figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
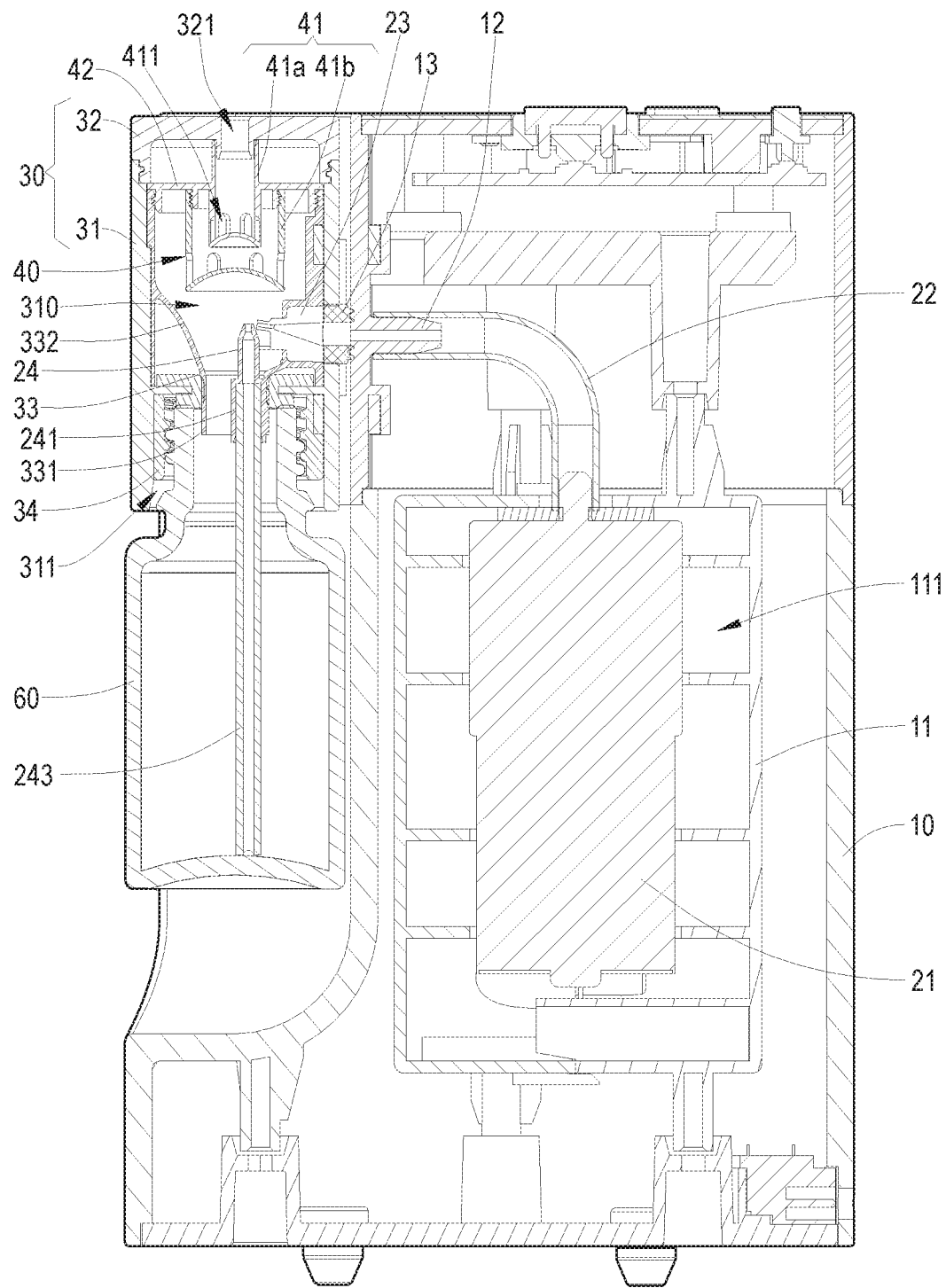
FIG. 1 is a sectional structure view of the essential oil atomizer provided by a first embodiment of the present invention.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

A conventional essential oil atomizer/nebulizer typically ejects a high-speed airflow to extract an essential oil from an essential oil bottle and to transfer the essential oil out of the atomizer into the surrounding atmosphere. However, this atomization method can result in larger droplets of essential oil in the atomized gas, so the atomization performance is poor and oil is inefficiently distributed. The large essential oil droplets can be wasted if they are dispensed. To reduce the waste of essential oils, a filter is often used for filtering the atomized airflow mixed with the essential oil droplets so as to recycle the essential oil droplets. However, since the space of the essential oil atomization chamber is generally small, the mixed airflow may directly hit and accumulate in an area of the sidewall of the atomization chamber facing the gas nozzle. With subsequent airflow hitting the same area, the essential oil droplets in the area can be blown and splashed to the filter, thereby blocking the filter, reducing the efficiency of filtration, and causing waste. These issues can be amplified and aggravated when the atomizer is moved from place to place because droplets or oil flow can gather and fall out of the machine when it is tilted sideways, turned upside down, and/or shaken.

Compared to conventional essential oil atomizers, airflow-guided essential oil reflux-type atomizers of the present invention can provide many beneficial effects. First, by providing the filter atomization mechanism in the atomization chamber, when an airflow is pumped out of the gas pump through the gas nozzle, the airflow extracts the essential oil from the essential oil bottle through the oil nozzle, and atomizes the essential oil to form a mixed airflow. When the mixed airflow passes through each of the filter housings of the filter atomization mechanism, successively larger essential oil droplets in the airflow are filtered by each of the filter housings to be recycled, thereby reducing waste of the essential oil, while smaller atomized essential oil droplets will pass through the through hole of each of the filter housings to be dispensed out the atomizer into the environment. When the essential oil droplets in the airflow are located in each of the through holes, the pressure difference between two sides of the filter housing can create an airflow in each of the through holes to re-atomize these essential oil droplets to improve the atomization performance.

Second, in embodiments having a guide board and filter in the atomization chamber, the mixed airflow (which includes a mixture of the airflow from a gas pump and essential oil from the oil bottle) can hit the guide board and be guided to flow upward to the filter atomization mechanism, where the larger essential oil droplets are filtered and recycled to reduce waste. At the same time, the guide board can also collect some of the essential oil droplets from the mixed airflow, reducing oil splashing which may block the filter to ensure filtration efficiency.

Furthermore, in order to help prevent the mess and expense of losing oil while the atomizer is moved around, embodiments of the present disclosure can comprise a set of sealing valves, gaskets, o-rings, and/or covers configured to limit or prevent oil from leaking from the atomizer and to help oil that moves within the atomizer to recollect in an oil receptacle when it is time to use the atomizer again in a proper orientation. In some cases, these seals can comprise a cover or sealing cap configured to block and plug an outlet opening in the housing from which atomized oil and gas (e.g., air) passes out of the atomizer. The seals can also include a one-way valve that permits air flow into the atomizer nozzle while preventing oil flow out of the atomizer nozzle in at least one direction and a seal configured to prevent leakage of oil between an oil receptacle and a portion of a housing receiving and connected to the receptacle.

Furthermore, embodiments of the present disclosure can improve the portability of an atomizer device. This can be done by reducing the dimensions of parts of the atomizer as compared to conventional atomizers, rearranging the parts to more efficiently use the space within the atomizer housing, adding portable gas and energy supply equipment, and sealing the device (e.g., as explained above) to limit or prevent oil leakage. In this manner, the atomizer device can be more easily transported and can be handheld (i.e., carried in the user's hands from place to place).

In some embodiments, the gas and oil nozzle assembly in the atomizer device can be configured to reduce oil wastage due to unnecessarily large oil droplets being carried by the gas out of the atomizer device. For example, in some cases, the oil nozzle assembly can comprise a gas nozzle that opens in a direction facing away from the outlet opening of an atomization chamber of the atomizer device or facing toward an oil receptacle or reservoir in the atomizer device. Thus, as gas is expelled from the gas nozzle and atomizes oil from the oil nozzle, the largest droplets of oil are driven along the direction of gas flow toward the oil receptacle and in a direction more than 90 degrees offset away from the axis of the outlet opening of the atomizer. However, sufficiently small droplets of oil can simultaneously be swept along with the gas flow that moves out of the outlet opening, so the atomized oil is still diffused and distributed out of the atomizer for droplets that are sufficiently small and light. Thus, the nozzle assembly can reduce the cost of oil by driving inefficiently atomized oil droplets back into the oil reservoir while allowing efficiently atomized droplets to flow out of the atomizer along the stream of gas.

It is noted that when a component is referred to as being "fixed to," "installed on," "arranged on" or "disposed on" another component, it can be directly or indirectly fixed on another component. When a component is referred to as being "connected to" another component, it can be directly or indirectly connected to the other component.

In addition, the terms "first" and "second" are for illustrative purposes only and should not be construed as indicating or implying a relative importance or indicating the quantity of technical features. Therefore, a feature that is qualified as "first" and "second" may expressly or implicitly include one or more of such a feature. In the description of the present invention, "multiple" means two or more, unless otherwise specifically defined.

Unless specified otherwise, it should be understood that, "length", "width", "upper", "lower", "front", "back", "left" and "right", "vertical", "horizontal", "top", "bottom", "inside", "outside" and other terms indicating the orientation or positional relationship are used to refer to orientation or positional relationship shown in the drawings, only for the purpose of facilitating and simplifying the description of the invention, instead of indicating or implying that the indicated device or component must have a specific orientation and constructed and operated in a particular orientation, and therefore cannot be construed as limiting.

In the description of the present invention, it should be noted that the terms "install," "connected," and "connect" should be interpreted broadly unless specifically defined or limited otherwise. For example, the components may be fixedly connected or they may be detachable connected, or integral connected. The connection can be mechanical or electrical. The connection can be direct or indirect (connected through an intermediary). It can also be the internal communication of two components or the interaction between two components. Those of ordinary skill in the art can understand the specific meanings of the above terms in the present disclosure according to specific circumstances.

Embodiment One

Figure 2:
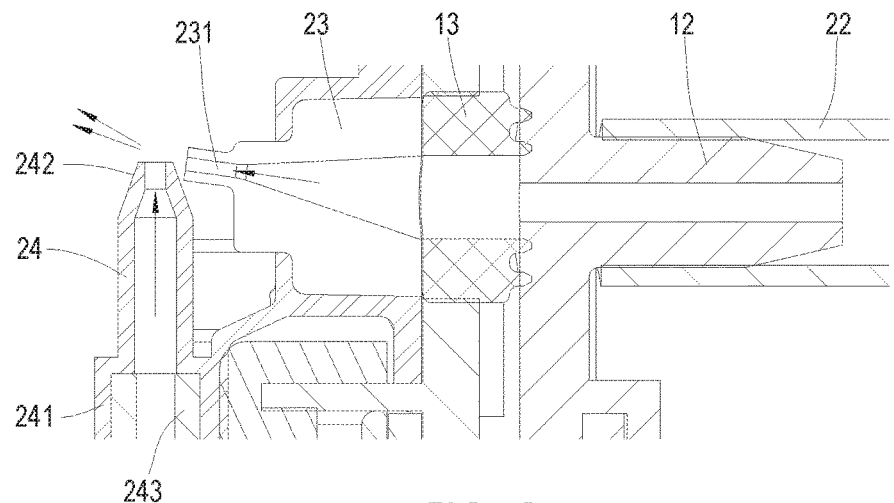
FIG. 2 is an enlarged view of the gas nozzle and the oil nozzle of the essential oil atomizer shown in FIG. 1.
Figure 3:
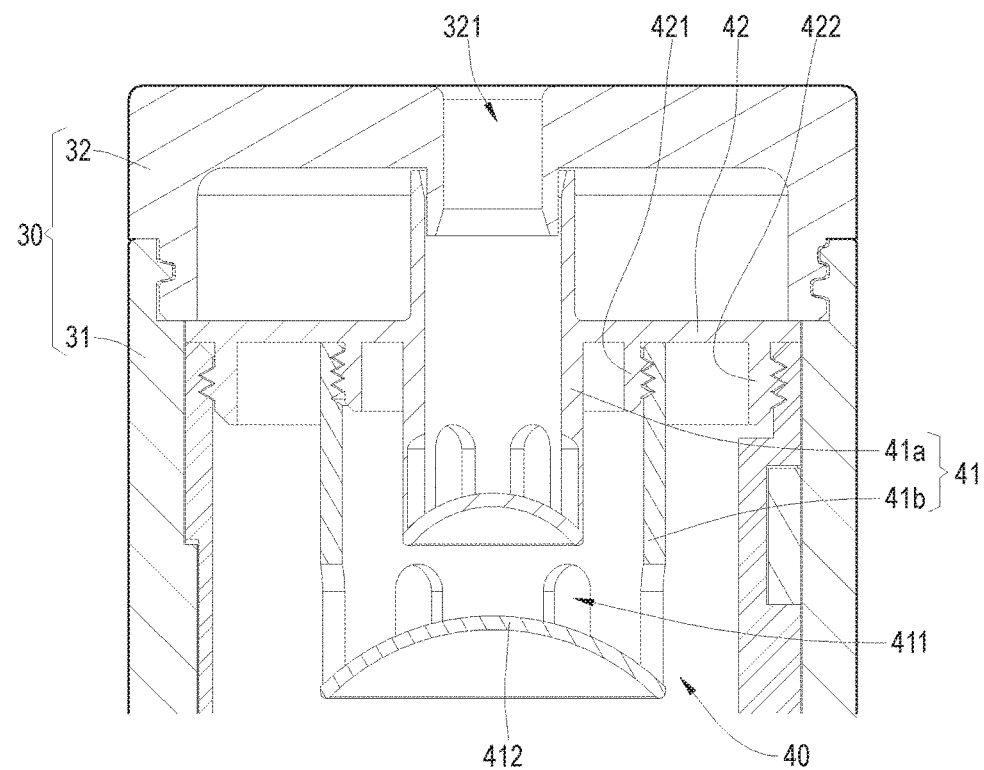
FIG. 3 is an enlarged view of the filter atomization mechanism of the essential oil atomizer shown in FIG. 1.
Figure 4:
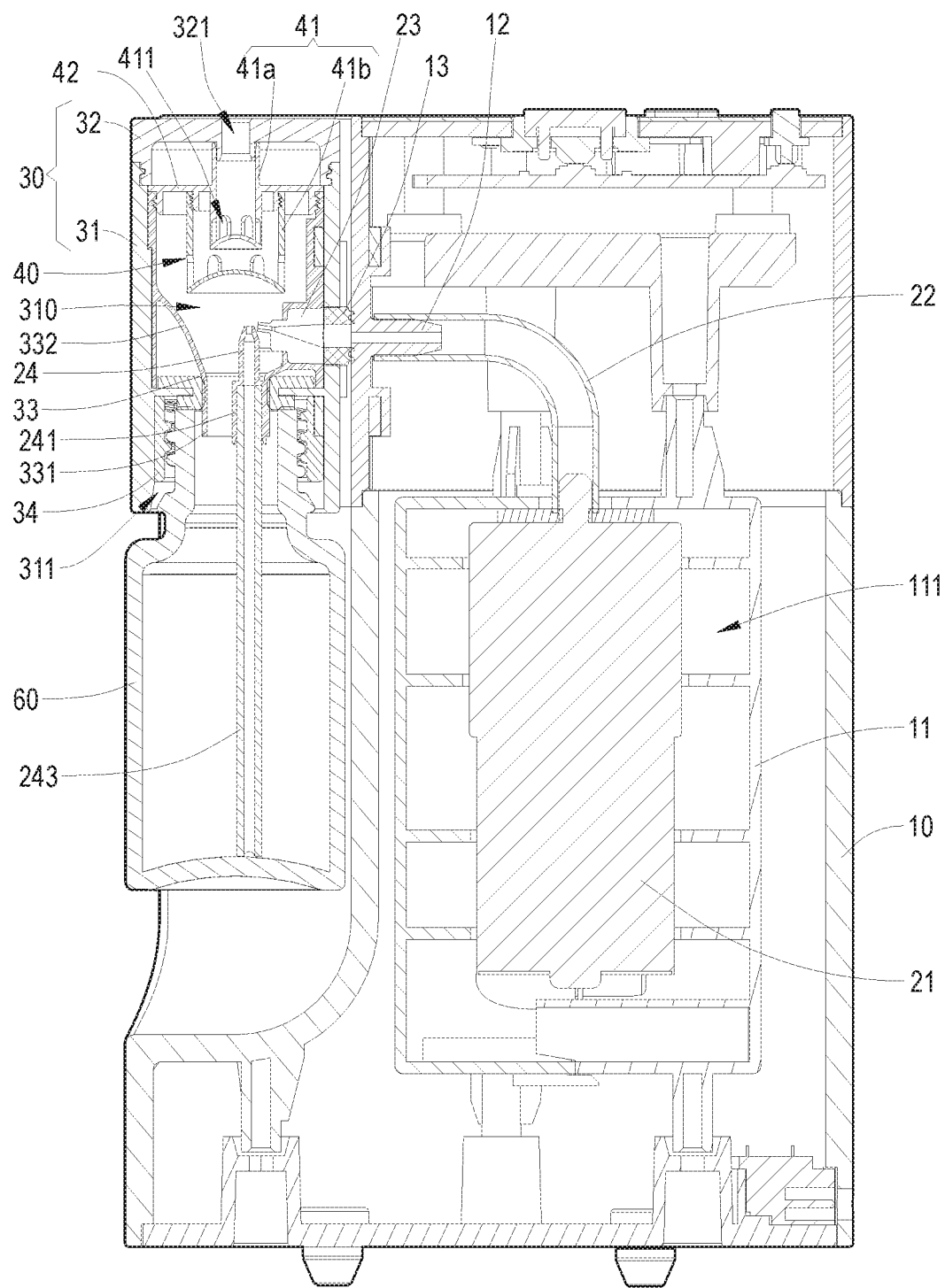
FIG. 4 is a sectional view of the essential oil atomizer provided by a second embodiment of the present invention.
Figure 5:
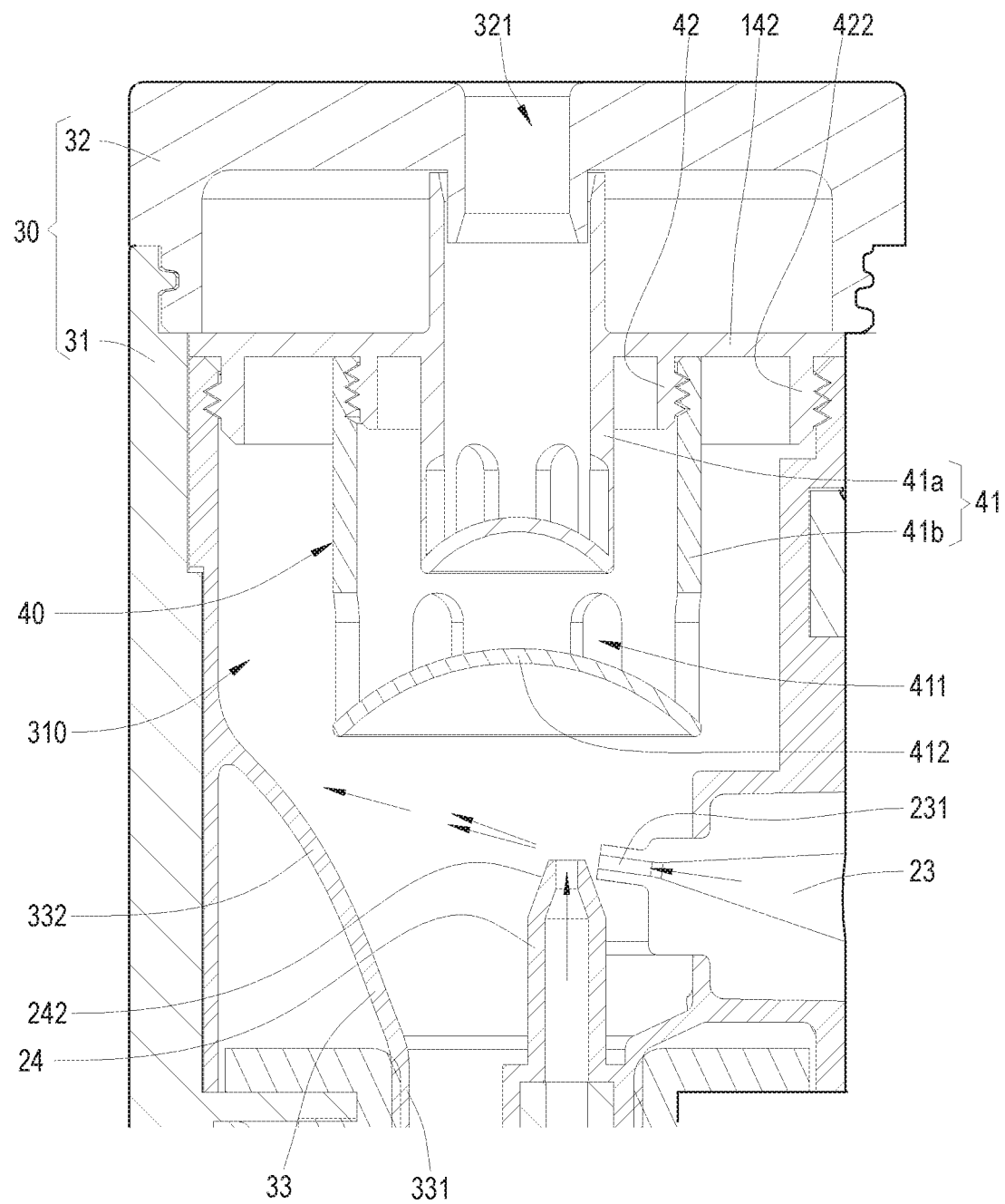
FIG. 5 is an enlarged view of the gas nozzle and the oil nozzle of the essential oil atomizer shown in FIG. 4

FIGS. 1 through 3 represent an embodiment of an essential oil reflux-type atomizer of the present invention. The essential oil reflux-type atomizer includes a chassis 10, a housing 30, a gas pump 21, a gas tube 22, a gas nozzle 23, an oil nozzle 24, and a filter atomization mechanism 40. The housing 30 includes an atomization chamber 310 and a dispensing opening 321 connected to the atomization chamber 310. A lower end of the housing 30 includes a connection opening 311 for cooperatively connecting the essential oil bottle 60. The housing 30 is installed on the chassis 10. The gas pump 21 is also installed in the chassis 10, which supports and protects the gas pump 21. One end of the gas tube 22 is connected to the gas pump 21, and the other end of the gas tube 22 is connected to the gas nozzle 23. The oil nozzle 24 is located at a position corresponding to the connection opening 311 so that when the connection opening 311 is connected to the essential oil bottle 60, the essential oil can be extracted from the essential oil bottle 60 through the oil nozzle. The upper end of the oil nozzle 24 is protruded into the atomization chamber 310. An outlet 231 of the gas nozzle 23 is located adjacent to the upper end of the oil nozzle 24 and is configured to direct an airflow exiting the gas pump to the upper end of the oil nozzle. Without wishing to be bound by theory, it is believed that, when the gas pump 21 provides high pressure airflow and ejects the airflow from the gas nozzle 23, a negative pressure is formed at the upper end of the oil nozzle 24 to extract essential oil from the essential oil bottle 60 via the oil nozzle 24. The extracted essential oil droplets can then be atomized by the high-speed airflow from the gas nozzle 23 to form a mixed airflow containing essential oil droplets, which increases the pressure in the atomization chamber 310. Because the connection opening 311 and the essential oil bottle 60 are connected, the high-pressure mixed airflow in the atomization chamber 310 will be forced through the dispensing opening 321 to be dispensed into the environment.

The filter atomization mechanism 40 is arranged in the atomization chamber 310 in the housing 30 and is supported by the housing 30. The filter atomization mechanism 40 is used to filter the essential oil droplets in the airflow flowing from the atomization chamber 310 to the dispensing opening 321. When the mixed airflow in the atomization chamber 310 flows toward the dispensing opening 321, it needs to pass through the filter atomization mechanism 40, where the mixed airflow may be filtered by the filter atomization mechanism 40 to recycle larger essential oil droplets and reduce the waste of essential oils while the smaller essential oil droplets will pass through the filter atomization mechanism 40 to be dispensed through the dispensing opening 321.

In general, the filter atomization mechanism 40 includes a plurality of (e.g., two, three, or four) filter housings 41. In some embodiments, when the airflow in the atomization chamber 310 flows toward the dispensing opening 321, it passes through the filter housings 41 successively. The lower ends (e.g., at the bottom of the cylinders) of the filter housings 41 include one or more (e.g., two, three, or four) through holes 411 for filtering the essential oil droplets in the airflow. When the airflow containing essential oil droplets passes through each of the filter housings 41 successively, the larger essential oil droplets in the mixed airflow are filtered by each of the filter housings 41 and can flow back to the oil bottle through the return funnel due to gravity. The smaller essential oil droplets can pass through the through hole 411 of each of the filter housings 41 to be dispensed through the dispensing opening 321. As discussed above, the airflow from the gas nozzle 23 increases the pressure in the atomization chamber outside the filter housings 41. Without wishing to be bound by theory, it is believed that the pressure difference at two sides of the filter housing 41 creates an airflow in each of the through holes 411, such that the essential oil droplets in the through holes 411 are re-atomized by the airflow to improve the atomization efficiency. As a result, using the plurality of filter housings 41 can better filter larger essential oil droplets, further reduce waste, and improve the efficiency of filtration. In addition, it is believed that, compared to a conventional system without a filter housing, using the filter housing 41 can better return the essential oil liquid accumulated therein, and avoid oil attachment to the filter atomization mechanism 40, and thus better recycle the filtered essential oil droplets and further reduce the waste of essential oils.

Compared to a conventional atomizer, the essential oil reflux-type atomizer of the present invention has one or more of the following beneficial effects: when the gas nozzle 23 blows out the airflow, essential oil is extracted from essential oil bottle through the oil nozzle 24, and mixed and atomized by the airflow to form a mixed airflow. When the mixed airflow passes through each of the filter housings 41 of the filter atomization mechanism 40 successively, the larger essential oil droplets in the airflow can be filtered by each of the filter housings 41 and recycled, thereby reducing waste of the essential oil. The smaller essential oil droplets can pass through each of the filter housings 41 and dispensed into the environment. The pressure difference between the two sides of the filter housing 41 creates an airflow in each of the through holes 411, therefore the essential oil droplets in the through hole 411 are re-atomized by the airflow to improve the atomization efficiency.

Further, FIGS. 1 and 3 show embodiments in which each of the filter housings 41 is cylindrical, the diameters of a plurality of the filter housings 41 are reduced successively, a plurality of the filter housings 41 are concentrically arranged, and the two adjacent filter housings 41 include an inner layer filter housing 41a is inserted into an outer layer filter housing 41b. The inner layer filter housing 41a is connected with the dispensing opening 321. The filter housings 41 are generally simple to manufacture, and easy to install. The filter housings 41 are located in the atomization chamber 310, facilitating the mixed airflow in the atomization chamber 310 to enter the filter housings 41 to be filtered and atomized. In addition, the filter housings 41 are arranged in a cylindrical shape, and one or more through holes 411 are arranged at the lower end of the filter housings 41. The inner layer filter housing 41a is inserted into the outer layer filter housing 41b. Without wishing to be bound by theory, it is believed that, when the mixed airflow enters the outer layer filter housing 41b from the through holes 411, it rotates and/or turbulently flows along the outer wall of the inner layer filter housing 41a. Thus, the atomized essential oil can rapidly diffuse, and the larger essential oil droplets will hit the outer surface of the inner layer filter housing 41a due to inertia to be blocked and filtered to improve the filtering effect. In addition, when the gas pump is not in use, the essential oil collected in the filter housings 41 forms larger droplets and returns to essential oil bottle 60 through the through holes of the filter housings 41 due to gravity and can be re-used. In some embodiments, a plurality of boards with holes (e.g., in addition to or in lieu of filter housings 41) may be used to filter the essential oil droplets in the atomization chamber. In other embodiments, the filter housings 41 may also be cup-shaped with the central part of the bottom arched downward.

In this embodiment, the number of the filter housings 41 is two, and the inner layer filter housing 41*a* is inserted into the outer layer filter housing 41*b*. In other embodiments, the number of the filter housings 41 can be three, four, or more.

Further, as shown in FIG. 3, the filter atomization mechanism 40 further includes a fixing board 42, which includes a plurality of connection rings 421 for connecting the upper ends of the filter housings 41 to the housing 30. With the connection rings 421, each of the filter housings 41 can be conveniently connected to the fixing board 42, either integrally or through threaded engagement. The fixing board 42 can be installed in the atomization chamber 310 so that the filter housings 41 can be installed in the atomization chamber 310. In some embodiments, the fixing board 42 includes a passing hole. The passing hole can be located in the innermost connection ring 421 so that when the innermost layer filter housing 41 is installed on the fixing board 42, the passing hole can receive the innermost layer filter housing 41, and thus the innermost layer filter housing 41 is connected with the dispensing opening 321.

Further, as shown in FIG. 3, the fixing board 42 can further include a fixing ring 422 around the connection rings 421. The fixing ring 422 can be connected with an inner wall of the atomization chamber 310. It is convenient to install and secure the fixing board 42 in the atomization chamber 310 through the fixing ring 422.

Furthermore, the fixing ring 422 may have installation threads. The inner wall of the atomization chamber 310 can have corresponding threads for threaded connection with the fixing ring 422.

Further, in some embodiments, one or more of the connection rings 421 may include a first thread, and the upper ends of the corresponding filter housings 41 may include a second thread corresponding to the first thread. The structure can be conveniently manufactured by methods known in the art. One or more of the filter housings 41 can be conveniently connected with the corresponding connection rings 421 through threaded engagement.

Further, as shown in FIGS. 1 and 2, the innermost layer filter housing 41 and the fixing board 42 are integrally formed. Forming the fixing board 42 integrally with the innermost layer filter housing 41 can ensure the connection strength between the innermost layer filter housing 41 and the fixing board 42. In this structure, the innermost connection ring 421 can be used as a sidewall of the inner layer filter housing 41 to reduce the space occupied. In other embodiments, the fixing board 42 and the innermost layer filter housing 41 can be two separate parts and can be connected through threaded engagement described above.

Further, as shown in FIGS. 1 and 2, a bottom board 412 of each of the filter housings 41 is curved, with the central part of the bottom board 412 arched upward. The through holes 411 are located at the lower end (e.g., defined by the sidewall and the bottom board) of the sidewall of the filter housings 41. The bottom board 412 of each of filter housings 41 is arched to allow the essential oil liquid collected in the filter housing 41 to flow toward the through holes 411 and be discharged back into the essential oil bottle 60.

Further, the through holes 411 of each of the filter housings 41 are located at the lower end of the sidewall (e.g., at the lower one-third of the sidewall) of each filter housing 41, making it convenient for manufacturing and also convenient for filtration and recycling of the essential oil droplets. Furthermore, when the bottom board 412 of a filter housing 41 has an upwardly arched arc surface, the arc surface can also guide the airflow flowing from each of the through holes 411 into the filter housing 41.

Further, the through holes 411 of two adjacent filter housings 41 can be mutually staggered. In such embodiments, when the airflow passes through the through hole 411 of the outer layer filter housing 41*b*, the larger essential oil droplets are blown onto the outer sidewall of the inner layer filter housing 41*a* to be blocked and collected to achieve better filtration. Smaller droplets have less mass and thus less inertia so that they can change directions more easily and stay with the airflow. In some embodiments, the through holes 411 in two adjacent filter housings 41 can have successively reduced diameters to filter larger essential oil droplets. For example, the diameters of the through holes 411 in the inner layer filter housing 41*a* can be smaller than those of the through holes 411 in the outer layer filter housing 41*b*. In some embodiments, the diameter of the though holes 411 of the innermost filter housing 41 ranges can be 1.6 mm-2.0 mm (e.g., 1.8 mm) while the diameter of the though holes 411 of the immediate outer filter housing 41 is can be 2.0 mm-2.4 mm (e.g., 2.2 mm). In such embodiments, the through holes 411 in the inner layer filter housing 41*a* and outer layer filter housing 41*b* can be either centrally aligned or staggered (i.e., not centrally aligned).

Further, in two adjacent filter housings 41, the bottom board of the inner layer filter housing 41*a* can be spaced from the bottom board 412 of the outer layer filter housing 41*b* so that the airflow in the gap between the inner layer filter housing 41*a* and the outer layer filter housing 41*b* can be increased, enhancing the filtration and recycling of the essential oil droplets.

Further, in two adjacent filter housings 41, the closest distance between the sidewall of the inner layer filter housing 41*a* and the sidewall of the outer layer filter housing 41*b* can range from at least 1.5 mm (e.g., at least 2 mm or at least 3 mm) to at most 10 mm (e.g., at most 9 mm or at most 8 mm). Without wishing to be bound by theory, it is believed that controlling the above distance to 1.5-10 mm can be important to minimize excessive noise when the essential oil atomizer is being used. In a preferred embodiment, the closest distance between the sidewalls of two adjacent filter housings 41 is 2.2 mm.

Further, as shown in FIGS. 1 and 2, the axial direction of the outlet 231 of the gas nozzle 23 is directed toward the top of the upper end of the sidewall 242 of the oil nozzle 24. The outlet axis of the gas nozzle and the outlet axis of the oil nozzle form an angle that is less than 90 degrees. When the airflow is ejected from the outlet 231 of the gas nozzle 23, the airflow can cover the upper end of the oil nozzle 24 to better form a negative pressure (e.g., due to Bernoulli effect) at the upper end of the oil nozzle 24, which can extract essential oil from the essential oil bottle 60. At the same time, the top of the sidewall 242 of the oil nozzle 24 can change the direction of the airflow ejected from the gas nozzle 23 (e.g., by blocking at least some of the airflow), thereby improving the atomization of the essential oil droplets drawn from the oil nozzle 24.

Further, the airflow ejected from the outlet 231 of the gas nozzle 23 is directed toward the top of the upper end of the sidewall 242 of the oil nozzle 24 from a lower position (e.g., the outlet 231 can be at a lower position than the oil nozzle 24). This arrangement can prevent the airflow ejected by the gas nozzle 23 from being blown into the oil nozzle 24, thereby facilitating extraction of the essential oil from the essential oil bottle and blowing the essential oil upward for better atomization. Further, in this embodiment, the sidewall 242 of the upper end of the oil nozzle 24 is conically shaped, guiding upward the airflow from the gas nozzle 23 so that the airflow can better atomize the essential oil drawn from the oil nozzle 24. In other embodiments, the sidewall 242 of the upper end of the oil nozzle 24 may also be a dome in shape.

Further, as shown FIG. 1, a lower end of the atomization chamber 310 includes a return funnel 33 with an outlet tube 331 at the bottom. The outlet tube 331 protrudes into the connection opening 311. The oil nozzle 24 is integrally connected to the outlet tube 331. When the connection opening 311 is connected with the essential oil bottle 60, the outlet tube 331 of the return funnel 33 is protruded into the essential oil bottle 60, so that the recycled essential oil droplets in the atomization chamber 310 can better return to the essential oil bottle 60.

Further, in this embodiment, the lower end of the return funnel 33 is connected with the inner wall of the atomization chamber 310, such that the essential oil liquid accumulated on the inner wall of the atomization chamber 310 can be easily returned to the essential oil bottle 60.

Further, as shown in FIG. 1, a lower end of the oil nozzle 24 is connected with a connection sleeve 241. An oil tube 243 can be detachably inserted in the connection sleeve 241 and can be in fluid communication with oil nozzle 24 such that essential oil can be extracted from essential oil bottle 60 to the atomization chamber 310 through the oil tube 243 and oil nozzle 24. In some embodiments, oil tubes 243 of different lengths can be used to fit different essential oil bottles 60, enhancing the adaptability of the design.

Further, as shown in FIG. 1 represent a connection tube 12 is arranged at the corresponding position of the chassis 10 to allow the gas tube 22 to be connected with the gas nozzle 23, thereby allowing airflow to travel from the gas pump 21 through the gas tube 22 and connection tube 12, and to be ejected from gas nozzle 23. The connection tube 12 is arranged in the chassis 10 such that the gas tube 22 can be securely attached to it to deliver airflow from the gas pump 21 into the atomization chamber 310.

Furthermore, in this embodiment, a sealing ring 13 is arranged between the gas nozzle 23 and the connection tube 12 to improve the sealing and minimize leaks of the connection so that substantially all the airflow in the gas tube 22 can flow through the gas nozzle 23. It is believed that this structure simplifies the manufacture and connection of the housing 30 and the chassis 10. In other embodiments, the gas nozzle 23 can also be directly connected to the gas tube 22 without using a connection tube 12. In some other embodiments, the gas nozzle 23 and the connection tube 12 can be integrally formed as a part of the chassis 10 (e.g., without using a sealing ring 13).

Further, as shown in FIGS. 1 and 3, the housing 30 includes a main housing 31 installed on the chassis 10 and an outer cover 32 installed on the main housing 31. The atomization chamber 310 is formed in the main housing 31, the outer cover 32 covers the atomization chamber 310. The outer cover 32 includes the dispensing opening 321 at the top of the housing 30. The connection opening 311 is arranged at a bottom of the main housing 31. This structure simplifies the manufacture of the housing 30 and the assembly of the parts. For example, it simplifies the installation of the oil nozzle 24, gas nozzle 23 and the filter atomization mechanism 40 onto the housing 30.

Further, as shown in FIGS. 1 and 3, the connection opening 311 is provided with a thread sleeve 34 for connecting the essential oil bottle 60. The thread sleeve 34 is arranged in the connection opening 311 to ensure easy installation and replacement of the essential oil bottle 60.

Further, as shown in FIG. 1, the chassis 10 includes a supporting frame 11. The gas pump 21 is installed on the supporting frame 11 for better fixation. The supporting frame 11 includes a plurality of heat dissipation channels 111 to improve the heat dissipation efficiency.

In some embodiments, the gas pump 21 can be a diaphragm pump. Of course, in other embodiments, the gas pump 21 can be other types of pumps, such as centrifugal pump, piston pump, and the like.

Embodiment Two

Referring to FIGS. 1 and 3, the essential oil reflux-type atomizer provided by embodiment two can have one or more of the following differences from embodiment one:

In some embodiments, a side of the atomization chamber 310 facing the gas nozzle 23 is provided with an optional guide board 332. The guide board 332 forms an inclined plane relative to the axial direction of an outlet 231 of the gas nozzle 23 and integrally connected with or formed on a sidewall of the atomization chamber 310. The guide board 332 is configured to guide the airflow jetted by the gas nozzle 23 upward. When the gas nozzle 23 ejects the air flow and extracts the essential oil to form the mixed airflow, the mixed airflow can flow towards the guide board 332 which can better guide the mixed airflow to the filter atomization mechanism 40, thereby facilitating filtration in filter atomization mechanism 40. In addition, the guide board 332 can also collect part of the essential oil droplets from the mixed airflow, reducing oil splashing (which may block the filter atomization mechanism 40) and ensuring filtration efficiency.

Further, the guide board 332 can be connected to an upper end of the return funnel 33. This structure can make it easier for the oil droplets accumulated on the guide board 332 to return to the essential oil bottle 60 through the return funnel 33, thereby improving the efficiency of the recycling process. Further, the guide board 332 may be integrally formed with the return funnel 33 to simplify manufacture, installation and fixation.

Further, in some embodiments, the guide board 332 is flat. In some embodiments, the guide board 332 is curved.

Further, the angle between an extension line of an outlet 231 axis of the gas nozzle 23 and the tangent line at the intersection of this extension line and the guide board 332 can range from at least 15 degrees (e.g., at least 20 degrees or at least 25 degrees) to at most 35 degrees (e.g., at most 30 degrees or at most 25 degrees). For example, the angle can be about 32 degrees. In this arrangement, the guide board 332 can better guide the airflow to the guide board 332, and reduce the impact of the airflow to the guide board 332.

Further, in one specific embodiment, the closest distance between the outermost filter housing 41 and the oil nozzle 24 is at least 2 mm (e.g., at least 3 mm or at least 4 mm). This distance can reduce the oil splashing on the filter housings 41 and avoid congestion at the filter atomization mechanism 40.

The other structures of the essential oil reflux-type atomizer in the present embodiment can be the same as the corresponding structures of the essential oil reflux-type atomizer in embodiment one, and the details will not be repeated here.

The aforementioned embodiments are only preferred embodiments of the present invention, and are not intended to limit the present invention. Any modification, equivalent replacement, improvement, and so on, which are made within the spirit and the principle of the present invention, should be included in the scope of the present invention.

Essential oil atomizers, including reflux-type atomizers, can have difficulty atomizing and diffusing essential oils that have high viscosity for high molecular weight. For example, in such cases, the essential oil can have difficulty traveling up an oil tube 243 or through an oil nozzle 24. Additionally, the oil can be less likely to atomize into droplets as result of airflow passing through the gas nozzle 23. Oil droplets that are atomized from the oil nozzle 24 can also be larger than desired and can therefore accumulate more easily within the atomization chamber 310 or on the filter housings 41.

Figure 6:
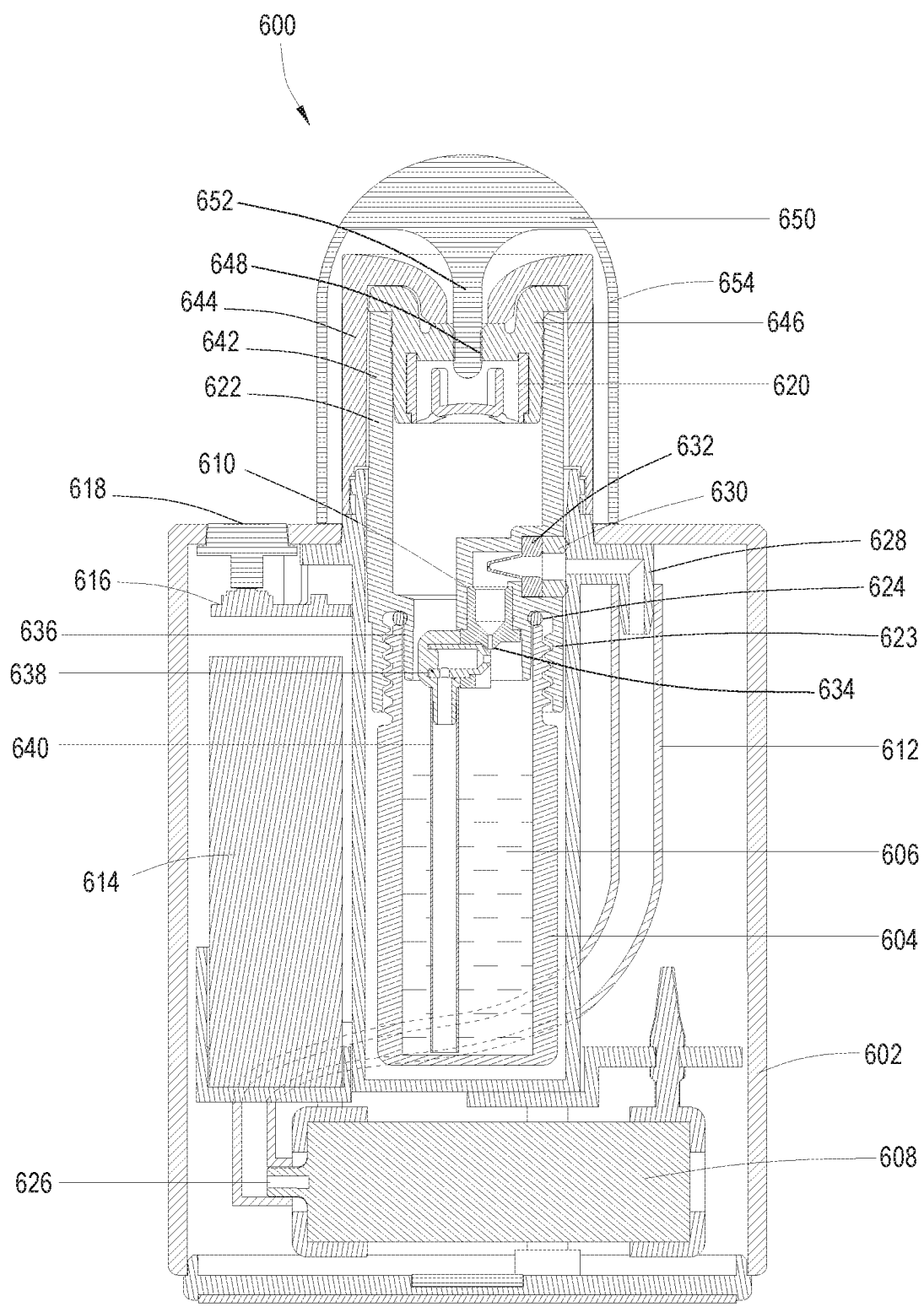
FIG. 6 is a sectional view of another embodiment of an essential oil atomizer.

Essential oil atomizers of the present disclosure can be used or modified to improve their portability, leak prevention, and ease of use. Accordingly, in some embodiments, the atomizers disclosed herein can include specialized sealing devices, mobile power sources, and components having reduced-size dimensions as compared to conventional atomizers. FIG. 6 shows a side cross-section of an example embodiment of a portable essential oil atomizer 600 of the present disclosure. Features and components of the atomizer 600 can be implemented in other embodiments disclosed herein. Additionally, features and components of other atomizers disclosed herein can be integrated into atomizer 600. In this embodiment, the atomizer 600 can comprise a housing 602 configured to contain an oil receptacle 604 for holding essential oil 606, a gas pump 608 to provide gas flow to a nozzle assembly 610 in the housing 602 via a gas line 612, an energy store 614 (e.g., battery), a control electronics unit 616 (e.g., a printed circuit board (PCB)) with a user input or output device 618 (e.g., a button, screen, touchscreen, switch, and/or similar device), a filter assembly 620 and outlet seal 646 with a central outlet 648 in a top end portion 644 of the housing 602, and an atomization housing 622 supporting the nozzle assembly 610.

The housing 602 may comprise a set of walls assembled together to contain and protect the other components of the atomizer 600. The housing 602 can be compact and capable of being carried by hand by a single user. In some embodiments, the housing 602 can be opened (e.g., by removing a panel of the housing 602 from other portions of the housing 602 or by removing the top end portion 644 from the lower portions of the housing 602) for maintenance or to remove, refill, or replace the oil receptacle 604 and/or atomization housing 622 and the components (e.g., 620, 646) held by the housing 622.

The oil receptacle 604 can comprise a bottle, tube, or cup configured to hold the essential oil 606 while the oil is being atomized by the atomizer 600. The oil receptacle 604 can alternatively be referred to as an oil reservoir, tank, or storage cavity in the atomizer 600. In some embodiments, the oil receptacle 604 can have an open and/or threaded top end portion that is configured to be received and retained by a lower end 623 of the atomization housing 622. In some embodiments, the lower end 623 can comprise threads to engage with a threaded top end of the oil receptacle 604. Other types of attachment mechanisms can also be used, such as, for example, a press fit, friction fit, interlocking parts, and other related connection mechanisms. A receptacle seal 624 (e.g., a resilient gasket or o-ring) can be positioned between and held in place by the oil receptacle 604 and the atomization housing 622. The receptacle seal 624 can limit or prevent leakage of oil from the receptacle 604 through the top end of the receptacle 604 at the interface with the lower end 623 of the atomization housing 622. The oil receptacle 604 and atomization housing 622 can apply opposing forces to the receptacle seal 624 to ensure that it remains in fluid-tight contact with each of them. In some embodiments, the receptacle seal 624 can be omitted, such as, for example, when the interface between the oil receptacle 604 and atomization housing 622 is sufficiently tight. In some embodiments, the oil receptacle 604 and atomization housing 622 can be formed as a single unit or single piece (e.g., by being molded, fastened, or welded together), and a receptacle seal 624 is unnecessary.

The gas pump 608 can be configured as a source of gas (e.g., air or compressed air) flow to the nozzle assembly 610 via the gas line 612. Thus, the gas pump 608 can comprise a vent outlet 626 in fluid communication with the gas line 612. The opposite end of the gas line 612 can be connected to a gas inlet 628 for the housing 602 that is connected to a gas inlet 630 for the atomization housing 622. Gas flow generated by the pump 608 through the vent outlet 626 can pass into the gas inlet 630 and then into the nozzle assembly 610 of the atomization housing 622 because the outer gas inlet 628 (i.e., the gas inlet of the housing 602) is in fluid communication with the inner gas inlet 630 (i.e., the gas inlet of the atomization housing 622). The perimeter of the inner gas inlet 630 can comprise a sealing material configured to prevent leakage of gas flow between the atomization housing 622 and the outer housing 602. In some embodiments, the atomization housing 622 and the outer housing 602 can be formed or fastened together in a manner wherein they function as a single piece, in which case a single gas inlet (e.g., 628) can receive the gas flow.

The nozzle assembly 610 can comprise a one-way valve 632 at the gas inlet 630. The one-way valve 632 can allow fluid flow in one direction (to the left in FIG. 6) while preventing fluid flow in the opposite direction (to the right in FIG. 6). The one-way valve 632 can therefore comprise a duck-bill valve, a check valve, or a similar valve structure that allows passage of fluid flow in one direction while restricting fluid flow in the opposite direction. Gas passing through the one-way valve 632 in the permissive direction can be redirected through the nozzle assembly 610 to a gas nozzle 634 used to accelerate, direct, focus, and expel the gas flow. In some embodiments, the one-way valve 632 can be omitted.

The gas nozzle 634 can have its longitudinal axis oriented in a substantially vertical/upward-downward direction, as shown in FIG. 6. The gas nozzle 634 can alternatively be referred to as having its outlet directed into the interior of the oil receptacle 604, toward the interior or bottom of the oil receptacle 604, toward the supply of oil 606, or directed away from the top end or outlet (e.g., 648) of the outer housing 602 or atomization housing 622. The gas nozzle 634 can be at least partially positioned within the top end of the oil receptacle 604, such as by having its outlet positioned lower than the top, open end of the receptacle 604. Thus, gas flow coming from the gas nozzle 634 can be directed into the receptacle 604, and any flow or spray that is laterally directed can be driven into contact with the receptacle 604, the oil 606, or an inner housing extension 636 of the atomization housing 622 that extends at least partially into the mouth of the receptacle 604. In some embodiments, the nozzle assembly 610 can be positioned with the gas and/or oil nozzles 634, 638 positioned above and/or outside the oil receptacle 604.

The nozzle assembly 610 can also comprise an oil nozzle 638 having an outlet positioned proximate to the outlet of the gas nozzle 634. Gas flow coming from the gas nozzle 634 can pass by the outlet of the oil nozzle 638 to create a low pressure zone at the outlet of the oil nozzle 638 and thereby draw oil 606 from the receptacle 604 through an oil tube 640 to be atomized and diffused into droplets as the oil comes into contact with the gas stream. The outlet of the oil nozzle 638 can be oriented substantially perpendicular to the outlet of the gas nozzle 634. For example, the gas nozzle 634 can comprise a longitudinal axis (i.e., the axis along the direction that gas exits the gas nozzle 634) that is substantially perpendicular to a longitudinal axis of the oil nozzle 638 along which the oil exits the oil nozzle 638 (i.e., horizontally in FIG. 6).

In this manner, the gas flow from the gas nozzle 634 can be driven initially and primarily downward, and oil droplets that are caught up in the gas flow can be initially driven downward in a direction away from the top, outlet end of the housing 602. The largest droplets of oil can therefore be driven in a direction toward the oil supply 606 and can therefore recollect in the receptacle 604 to be recirculated through the oil tube 640. This can be beneficial to improve the diffusion efficiency of the device (i.e., the efficiency of the atomizer 600 to atomize the oil and distribute it across large distances from the atomizer 600) because larger, heavier droplets of oil are generally not expelled from the opening of the atomizer 600 and are instead recycled until they are sufficiently broken up to be able to ride the gas current from the gas nozzle 634 up through the atomization housing 622 and through the top end portion 644 of the housing 602. In order to pass out of the atomization housing 622, the gas current can, after passing downward across the oil nozzle 638, flow around and up through the atomization housing 622 to the top end of the housing 602. However, as explained above, large droplets of oil can be too heavy to rise with that gas current up through the top of the housing 602 or can get stuck to the interior of the atomization housing 622 or nozzle assembly 610 and eventually regather in the receptacle 604 instead of passing out of the housing 602. In some embodiments, the filter assembly 620 can be removed from the atomizer 600 due to the effectiveness of the collection of large droplets due to gravity and the direction of gas flow from the gas nozzle 634. Thus, a filter assembly 620 can be made optional due to the design and orientation of outlets of the nozzle assembly 610. However, a filter assembly 620 can in some embodiments be positioned in the atomizer 600 to further reduce and refine the droplet size of the atomized oil that escapes the atomizer and to help reduce noise produced by the atomizer 600.

The nozzle assembly 610 can also beneficially be positioned at least partially within the receptacle 604 to reduce the overall height and internal volume needed for atomizing oil in the atomization housing 622 since at least part of the atomization of the oil takes place within the receptacle 604. Thus, rather than having a receptacle 604 with a relatively unused, open area or void in the top end thereof, the nozzle assembly 610 can be positioned in that top end to reduce the amount of space needed for the nozzle assembly 610 elsewhere in the atomizer 600. Additionally, the lower end 623 of the atomization housing 622 can have an outer diameter substantially equal to, or slightly smaller than, the inner diameter of the receptacle 604 at its top end or where the receptacle 604 interfaces with the atomization housing 622. Accordingly, the lower end 623 can help stabilize the receptacle 604 relative to the atomization housing 622 and thereby improve the effectiveness of the receptacle seal 624 by limiting relative movement between the receptacle 604 and the atomization housing 622.

The energy store 614 can comprise an energy storage device such as a battery or fuel cell. In some embodiments, the energy store 614 can be replaced by or supplemented by a generation device such as a fuel-based generator, a solar panel, or a wind generator. The energy store 614 (or generation device) can be used to provide energy or power to drive the gas pump 608 and can be in electrical communication with the control electronics unit 616 to power a PCB, provide power to an output device (e.g., a light, display, or screen), or control the output of the gas pump 608.

The filter assembly 620 can be positioned within a top end 642 of the atomization housing 622 and a top end portion 644 of the housing 602. The top end 642 can have an outlet seal 646 with a central opening 648 that allows passage of gas and atomized oil filtered by the filter assembly 620. The outlet seal 646 can be positioned in the top end 642 of the atomization housing 622 and can support and hold the filter assembly 620 in place in the opening. The outlet seal 646 can comprise the central opening 648 through which gas and atomized oil can pass when an outer cover 650 is removed. The top end portion 644 of the housing 602 can be referred to as an inner cover and can have a central opening aligned and concentric with the central opening 648, as shown in FIG. 6. The top end portion 644 can hold the outlet seal 646 and atomization housing 622 in place relative to the housing 602. In some embodiments, the top end portion 644 portion of the outer housing 602 and the outlet seal 646 can be a single, integral piece with a single central opening 648. In some embodiments, multiple vent openings like central opening 648 can be positioned in and around the top end portion 644 and outlet seal 646.

In some embodiments, the atomization housing 622 and oil receptacle 604 can be removable from the housing 602 as a single unit. For example, the top end portion 644 or inner cover can be removed at its interface with the housing 602 (near the bottom of the outer flange 654), and the atomization housing 622 and receptacle 604 can be pulled upward and out of the housing 602 along with the nozzle assembly 610, filter assembly 620, and outlet seal 646. In this manner, all of these removed parts can be quickly and easily replaced, refilled, or otherwise adjusted or changed without having to take apart the rest of the housing 602. For example, the removability of these components as a single unit can allow the user to use different atomization housings 622 with different types of essential oils, thereby preventing cross-contamination, reducing the need to clean the atomization housing 622 when new oil is used, implementing a nozzle assembly 610 with higher or lower air or oil flow (e.g., to accommodate the atomization of oils having different viscosities, fragrance strengths, prices, etc.) or to customize the rate of diffusion or atomization of the oils used. Thus, in some embodiments, a first atomization housing 622, nozzle assembly 610, and oil receptacle 604 can be removed and exchanged for a second, different atomization housing, nozzle assembly, and oil receptacle that have different dimensions (e.g., oil storage capacity, central opening sizes, or nozzle sizes), mechanical properties (e.g., resilience), oil, or other properties and features.

The outer cover 650 can comprise a plunger portion 652 configured to be insertable into the central opening 648 of the outlet seal 646, as shown in FIG. 6. The plunger portion 652 can have an elongated shape having an outer diameter substantially equal to or slightly larger than the central opening 648. In this fashion, the plunger portion 652 can be inserted into the central opening 648 to seal the opening and thereby prevent oil (e.g., 606) from leaking out of the central opening 648 when the orientation of the atomizer 600 is turned or inverted. The plunger portion 652 can comprise a rigid material configured to elastically deform the outlet seal 646 when inserted into the central opening 648 to ensure a tight friction fit between the outer cover 650 and the outlet seal 646. In some embodiments, the plunger portion 652 can also comprise an elastically resilient material. In some configurations, the plunger portion 652 comprises an elastically resilient material and outlet seal 646 comprises a rigid material. Thus, the plunger portion 652 can deform (i.e., resiliently expand) the central opening 648 in the outlet seal 646 when it is moved into a first position sealing the opening 648, the outlet seal 646 can deform (i.e., resiliently compress or stretch) the plunger portion 652 in that position, or the seal 646 and plunger portion 652 can both deform when they are assembled. The deformation of these parts can ensure that there is a tight, friction fit between the parts that prevents leakage or unintended separation of the parts from each other.

The outer cover 650 can also comprise an outer flange 654 configured to surround the top end portion 644 of the housing 602. The outer flange 654 can help protect the top end portion 644 from damage as the atomizer 600 moves around, such as when the atomizer 600 is positioned in a bag or suitcase and the outer cover 650 is subjected to lateral forces on the outer flange 654.

Other aspects of the present disclosure relate to methods for making and using the essential oil atomizers disclosed herein. For instance, one such method includes positioning a plunger or stopper in a top end of an atomizer housing or seal of the atomizer housing, positioning a valve in a gas inlet for an atomizer housing, or sealing an interface between an oil receptacle (e.g., 604) and an atomization housing (e.g., 622) or outer housing (e.g., 602) of the atomizer. Another example method embodiments can include positioning a gas nozzle within an atomizer such that the gas nozzle is configured to expel air in a direction oriented into an oil receptacle or in a greater than 90-degree offset (e.g., opposite) direction from an atomization venting opening (e.g., central opening 648) of the atomizer. The expelled air can atomize a supply of oil (e.g., at the oil nozzle 638) and at least initially drive the atomized oil in a direction facing at least partially opposite the atomization venting opening of the atomizer, as explained in detail above. Thus, atomized oil and gas can be driven initially downward, toward the oil supply or an oil reservoir, and can then rise along with the gas flow in the opposite direction (i.e., toward the atomization venting opening) after large oil droplets or splatter is removed from the mix of atomized oil and gas.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. An essential oil atomizer, comprising:
   a housing having an end opening configured to connect to an oil receptacle, the housing having an outlet opening;
   a nozzle assembly configured to be in fluid communication with a gas source and configured to be in fluid communication with oil in the oil receptacle to atomize the oil with gas from the gas source;
   a cover having a plunger portion movable between a first position in which the outlet opening is unsealed and a second position in which the outlet opening is sealed by the plunger portion, wherein in the second position, the plunger portion is aligned and concentric with the outlet opening and the end opening of the housing; and
   a filter assembly;
   wherein the housing comprises an outlet seal, the outlet opening is defined in the outlet seal, and the filter assembly is held in place between the outlet opening and the nozzle assembly by the outlet seal.

2. The essential oil atomizer of claim 1, further comprising:
   the gas source, the gas source comprising a gas pump;
   an energy source positioned in the housing and electrically connected to the gas pump;
   wherein gas emitted from the gas pump is configured to pass through the nozzle assembly to atomize oil in the nozzle assembly;
   wherein atomized oil and gas is movable through the outlet opening when the cover is in the first position.

3. The essential oil atomizer of claim 1, wherein the cover comprises an outer shell portion surrounding a portion of the housing when the cover is in the second position.

4. The essential oil atomizer of claim 1, further comprising an inner cover positioned on a portion of the housing bearing the outlet opening.

5. The essential oil atomizer of claim 1, wherein at least one of the outlet opening and the cover are configured to deform when the outlet opening is sealed.

6. The essential oil atomizer of claim 1, wherein the nozzle assembly comprises an inlet, wherein a one-way valve is configured to prevent gas or oil flow through the inlet.

7. An essential oil atomizer, comprising:
   a housing having a first end, a second end positioned opposite the first end, and an outlet opening through the first end, wherein the housing is attachable to an oil receptacle;

a nozzle assembly having:
  an oil inlet configured to connect to an oil source;
  an oil nozzle connected to the oil inlet and having an oil nozzle longitudinal axis;
  a gas inlet configured to connect to a gas source; and
  a gas nozzle connected to the gas inlet and having a gas nozzle longitudinal axis, wherein the gas nozzle longitudinal axis is oriented substantially perpendicular to the oil nozzle longitudinal axis to output gas across the oil inlet to atomize oil at the oil nozzle, the gas nozzle being configured to expel gas toward the second end of the housing and into an interior of the oil receptacle; and
a one-way valve configured to prevent fluid flow through the oil inlet or the gas inlet.

8. The essential oil atomizer of claim 7, further comprising:
  the gas source, the gas source comprising a gas pump positioned in the housing;
  an energy source positioned in the housing and electrically connected to the gas source;
  wherein atomized oil and gas is movable through an outlet in the housing.

9. The essential oil atomizer of claim 7, further comprising the gas source connected to the gas inlet, the gas source configured to supply gas through the one-way valve.

10. The essential oil atomizer of claim 7, wherein the one-way valve is a check valve or a duckbill valve.

11. The essential oil atomizer of claim 7, wherein the one-way valve is positioned in the gas inlet.

12. The essential oil atomizer of claim 7, wherein the one-way valve is configured to prevent fluid flow of oil from the oil source through the gas inlet.

13. The essential oil atomizer of claim 7, further comprising a cover, wherein the housing comprises an outlet, the cover being configured to seal fluid communication through the outlet.

14. An essential oil atomizer, comprising:
  a housing having a first end, a second end positioned opposite the first end, and an outlet opening through the first end, wherein the housing is attachable to an oil receptacle;
  a nozzle assembly positioned in the housing and comprising a gas nozzle and an oil nozzle, a longitudinal axis of the gas nozzle being oriented perpendicular to a longitudinal axis of the oil nozzle, the gas nozzle being configured to expel gas toward the second end and configured with a nozzle outlet to open into an interior of the oil receptacle;
  wherein oil in the oil nozzle is configured to be atomized by gas from the gas nozzle and to pass through the outlet of the housing.

15. The essential oil atomizer of claim 14, further comprising:
  a gas pump located in the housing and connected to the gas nozzle;
  a cover configured to reversibly seal the outlet at the first end; and
  a valve preventing fluid flow from the oil nozzle to the gas pump.

16. The essential oil atomizer of claim 14, wherein the housing is attachable to the oil receptacle with the gas nozzle and the oil nozzle at least partially within the oil receptacle.

17. The essential oil atomizer of claim 14, wherein the gas nozzle is oriented substantially perpendicular to the oil nozzle.

18. The essential oil atomizer of claim 14, further comprising a valve to prevent fluid flow through an inlet of the nozzle assembly.

19. The essential oil atomizer of claim 14, wherein the oil nozzle comprises an oil outlet having a substantially horizontal longitudinal axis.

* * * * *